United States Patent
Marshall et al.

(10) Patent No.: US 6,951,664 B2
(45) Date of Patent: Oct. 4, 2005

(54) METHOD OF MANUFACTURING AN IMPLANTABLE DEVICE FEEDTHROUGH ASSEMBLY

(75) Inventors: Mark T. Marshall, Forest Lake, MN (US); James R. Svensk, Coon Rapids, MN (US); Kenneth E. Cobian, St. Anthony, MN (US); Richard D. Ries, Stillwater, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 10/875,459

(22) Filed: Jun. 24, 2004

(65) Prior Publication Data

US 2005/0095352 A1 May 5, 2005

Related U.S. Application Data

(62) Division of application No. 10/695,715, filed on Oct. 29, 2003, now Pat. No. 6,903,268.

(51) Int. Cl.$^7$ .............................. B05D 3/00; A61L 31/00
(52) U.S. Cl. ...................................... 427/2.24; 427/402
(58) Field of Search ................................ 427/2.24, 402

(56) References Cited

U.S. PATENT DOCUMENTS

| | | | | |
|---|---|---|---|---|
| 4,424,551 A | * | 1/1984 | Stevenson et al. | 361/302 |
| 5,333,095 A | * | 7/1994 | Stevenson et al. | 361/302 |
| 5,564,434 A | | 10/1996 | Halperin et al. | 128/478 |
| 6,275,369 B1 | * | 8/2001 | Stevenson et al. | 361/302 |

* cited by examiner

*Primary Examiner*—Brian K. Talbot
(74) *Attorney, Agent, or Firm*—Girma Wolde-Michael; Michael C. Soldner

(57) ABSTRACT

An implantable component including a feedthrough assembly and a method for forming the feedthrough assembly wherein a coating forming a fluid barrier over an insulator, an insulator-to-terminal pin interface and an insulator-to-ferrule interface is incorporated.

23 Claims, 7 Drawing Sheets

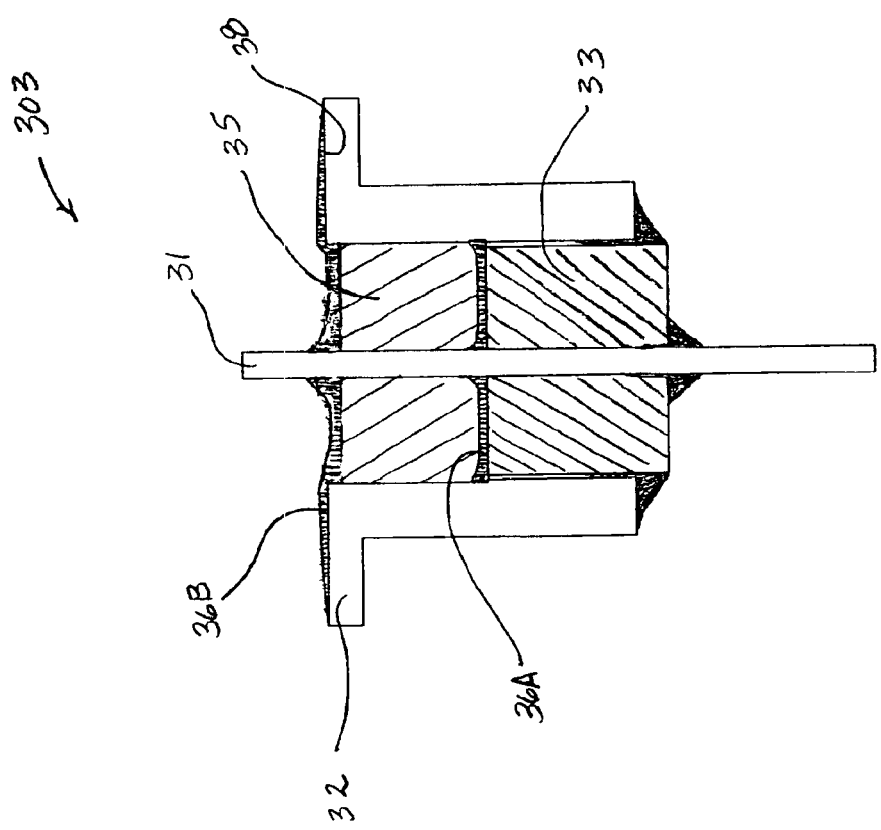

METHOD OF MANUFACTURING AN IMPLANTABLE DEVICE FEEDTHROUGH ASSEMBLY

This is a divisional application of U.S. Ser. No. 10/695,715, filed Oct. 29, 2003, now U.S. Pat. No. 6,903,268, entitled "Implantable Device Feedthrough Assembly".

TECHNICAL FIELD

The present invention relates to implantable devices incorporating electrical feedthrough assemblies, and to their method of fabrication. More particularly, the present invention relates to feedthrough assemblies that incorporate a backfill providing a barrier to moisture and ion ingress.

BACKGROUND

Electrical feedthrough assemblies provide a conductive path extending between the interior of a hermetically sealed container and a point outside the container. Some implantable medical device components such as biorhythm sensors, pressure sensors, and pulse generators are contained as such and incorporate feedthrough assemblies. The conductive path comprises a conductive pin or terminal that is electrically insulated from the container. Many feedthrough assemblies, which are known in the art, include the terminal, a ferrule surrounding the terminal, an insulating body such as a glass or ceramic material for positioning and insulating the pin within the ferrule, and an epoxy backfill of the ferrule, over the insulator and around the terminal.

Feedthrough corrosion may be encountered with any medical device components possessing a terminal that comes into contact with body fluids or electrolytes, if fluid leak paths form in the backfill or at the interface of the backfill with the terminal and or ferrule. Furthermore, loading of the feedthrough under a constant DC bias in the presence of moisture and contamination or electrolyte can accelerate corrosion and the formation of dendrites. A build up of corrosion by-products within the feedthrough can also result in additional stresses, which may form cracks within the insulator. Accordingly, it is desirable to provide a more durable feedthrough backfill for medical device components, which is not susceptible to formation of fluid leak paths.

BRIEF DESCRIPTION OF THE DRAWINGS

The following drawings are illustrative of particular embodiments of the invention and therefore do not limit its scope, but are presented to assist in providing a proper understanding of the invention. The drawings are not to scale (unless so stated) and are intended for use in conjunction with the explanations in the following detailed description. The present invention will hereinafter be described in conjunction with the following drawing figures, wherein like numerals denote like elements.

FIGS. 3B–E are section views of electrical feedthrough assemblies according to alternate embodiments of the present invention representing groups tested against the control depicted in FIG. 3A.

DETAILED DESCRIPTION

The following detailed description is merely exemplary in nature and is not intended to limit the invention or the application and uses of the invention. Furthermore, there is no intention to be bound by any expressed or implied theory presented in the preceding technical field, background or the following detailed description.

Figure 1:
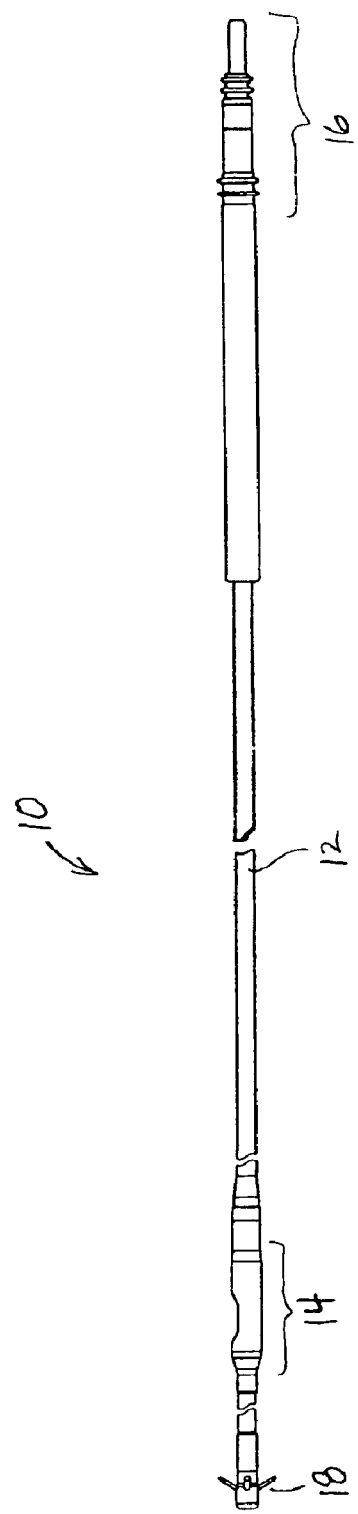
FIG. 1 is a plan view of an exemplary medical lead including a component according to one embodiment of the present invention.

FIG. 1 is a plan view of an exemplary medical lead including a component according to one embodiment of the present invention. FIG. 1 illustrates a lead 10 including a lead body 12 extending between a connector 16, terminating a proximal end, and a pressure sensor component 14 coupled in proximity to a distal end, which includes tines 18 to facilitate fixation in a body. Construction details for such a lead as is illustrated in FIG. 1 are well known to those skilled in the art and one example of a similar lead including a pressure sensor component is described in commonly assigned U.S. Pat. No. 5,564,434, the teaching of which is incorporated herein. According to one embodiment, pressure sensor component 14 includes a feedthrough assembly incorporating characteristics of the present invention, which are further described in conjunction with FIG. 2.

Figure 2:
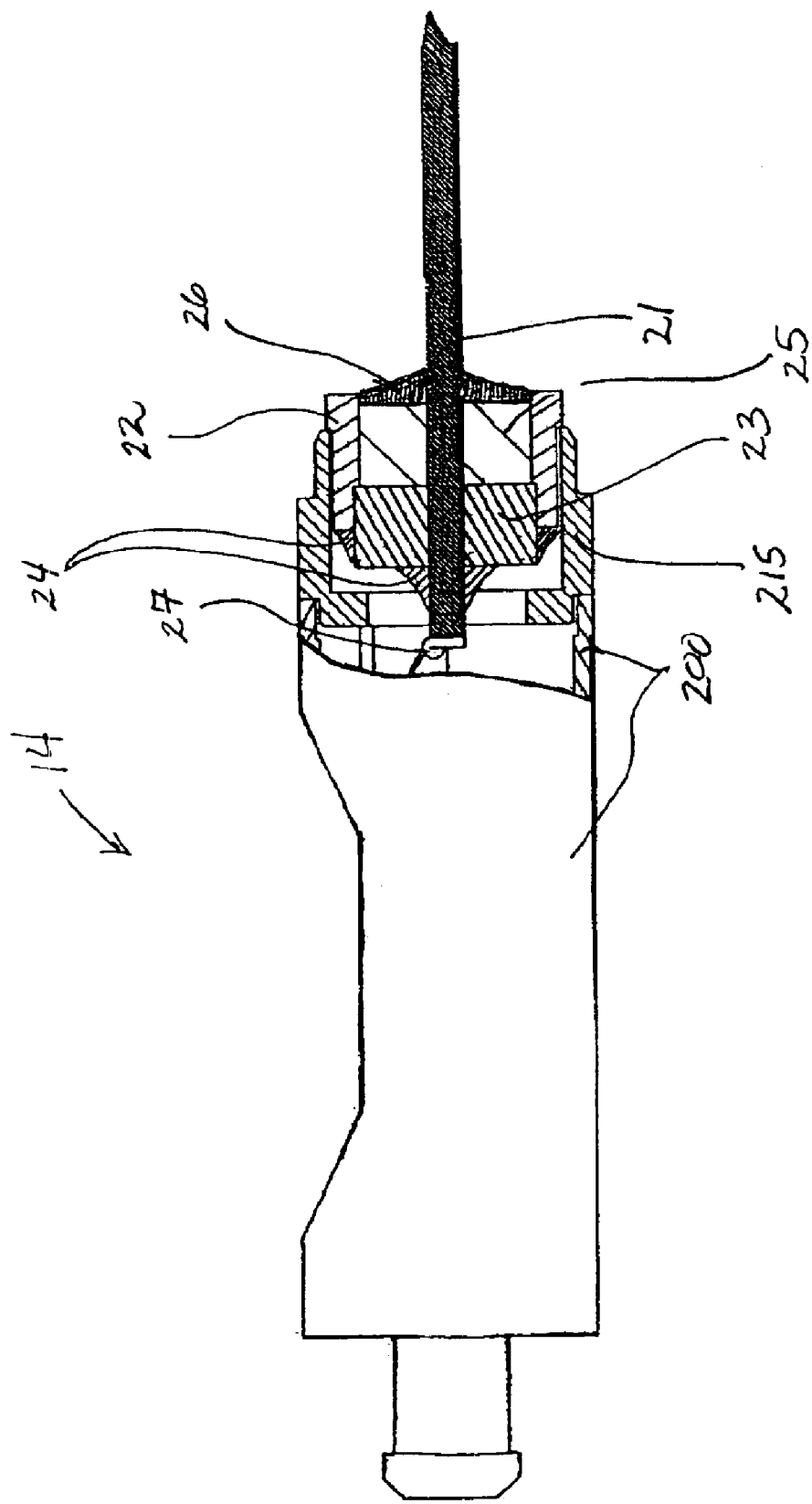
FIG. 2 is a partial section view of the component, included in the lead shown in FIG. 1, according to one embodiment of the present invention.

FIG. 2 is a partial section view of sensor component, included in lead 10 shown in FIG. 1, illustrating a feedthrough assembly according to one embodiment of the present invention. FIG. 2 illustrates sensor component 14 including a housing 200 and an adapter ring 215 surrounding a feedthrough assembly, which serve to electrically and mechanically couple sensor component 14 to lead body 12. FIG. 2 further illustrates the feedthrough assembly including a ferrule 22 and a terminal pin 21 isolated from one another by an insulator 23 wherein a fluid tight seal is formed by a metal braze 24 formed between insulator 23 and ferrule 22 and between insulator 23 and terminal pin 21; such an assembly is well known in the art. In this exemplary embodiment insulator 23 is ceramic, such as sapphire, but according to alternate embodiments an insulator may be glass or ceramic-containing material or other electrically-insulative material such as diamond, ruby, zinc oxide or even high dielectric polymers such as polyimides. Over time fluids may leak into micro-scale gaps between insulator 23 and terminal 21 or between the insulator 23 and ferrule 22 and metal braze 24 helps to prevent such leakage; a metal used for braze is any suitable corrosion resistant metal, one example of which is gold.

According to the embodiment illustrated in FIG. 2, ferrule 22 is a sleeve having an annular configuration suitable for coupling to ring 215, which is in turn coupled to housing 200; appropriate coupling means include, but are not limited to welding, adhesive bonding and soldering. Suitable materials from which ferrule 22 may be formed include, but are not limited to titanium, niobium, platinum, molybdenum, tantalum, zirconium, vanadium, tungsten, iridium, rhodium, rhenium, osmium, ruthenium, palladium, and any combination thereof. In a typical installation, as illustrated, one end of terminal pin 21 extends into housing 200 to electrically connect with at least one internal contact 27 while another end of terminal pin 21 couples to a lead conductor (not shown) exterior of housing 200. Suitable materials from which terminal 21 may be formed include but are not limited to niobium, titanium, tantalum, platinum, iridium, zirconium, nitrides of the preceding metals, alloys of the preceding metals, and other bio-stable conductive metals. Preferably, the terminal 21 is manufactured using a refractory metal, examples of which include, but are not limited to, molybdenum, tungsten, tantalum, rhenium, and niobium.

As is further illustrated in FIG. 2, insulator 23 surrounds a portion of the length of terminal pin 21 within ferrule 22 and the feedthrough assembly further includes a backfill over insulator surrounding another portion of terminal pin 21 within ferrule. According to one embodiment of the present invention the backfill includes a layer of filler 25 and a coating 26; coating 26 forms a fluid barrier over filler 25, insulator 23 and the interfaces with ferrule 22 and terminal 21. It should be noted that the term "coating" in the context of the present invention is defined as a layer of material conforming and adhering to underlying surfaces with which it comes into contact and being free of significant discontinuities and or contamination that may compromise the integrity of the fluid barrier formed by the coating over time. The scope of the present invention encompasses coatings forming fluid barriers over insulators and interfaces between insulators and ferrules and between insulators and terminal pins in cases where a coating is adhered directly to an insulator and in cases where an intervening layer or layers of filler material are present in between a coating and an insulator.

According to one embodiment of the present invention, filler 25 illustrated in FIG. 2 is an epoxy; according to another embodiment, filler 25 is a silicone. According to one embodiment of the present invention, coating 26 illustrated in FIG. 2 is a polymer/solvent solution when it is applied. Examples of suitable polymers include but are not limited to silicone, polyimides, and fluorosilicones. A solvent combined with the polymer of coating 26 must be sufficiently miscible with the polymer to allow the polymer to uniformly contact and adhere to the insulation material and metals of the feedthrough assembly. Some examples of suitable solvents for silicone and fluorosilicones are hexane and heptane and some examples of suitable solvents for polyimides are N-methyl-pyrrolidinone, N,N'-dimethyl-acetamide and N,N'-dimethyl-formamide.

A polymer/solvent solution can be dispensed to form coating 26 in any conventional manner. One exemplary way to dispense the polymer/solvent solution is through a syringe having a small stub adaptor needle coupled thereto. After the polymer/solvent solution is applied, between approximately 2 and approximately 60 minutes, the solvent evaporates leaving the polymer adhered to underlying surfaces of a feedthrough assembly, for example, as illustrated in FIG. 2, exposed surfaces of filler 25, terminal pin 21 and ferrule 22, thus providing a fluid barrier over insulator 23 and the interfaces between insulator 23 and ferrule 22 and between insulator 23 and terminal pin 21.

According to some embodiments of the present invention, a maximum thickness of coating 26 is maintained at less than approximately 0.01 inch; such a restriction on coating thickness may prevent bubbles from forming within coating 26 which could impede contact between coating 26 and any irregularities that may be present on exposed underlying surfaces, which coating 26 contacts. Furthermore such a thickness may also facilitate conformance of coating 26 within voids of underlying surfaces, which coating contacts.

Although FIGS. 1 and 2 describe a pressure sensor component integrated into an implantable lead, it should be understood that feedthrough assemblies including aspects of the present invention are not limited to leads, but may be incorporated into components of any type of implantable medical device.

EXAMPLES

Groups of samples according to alternate embodiments of the present invention were assembled for testing against control groups. Each of the groups included 4 samples, which were subjected to a constant 4-volt DC bias within a 2% saline solution environment in order to determine feedthrough lifespan. A sample was designated as failing the test whenever a dendrite was observed during visual examination or a short was noted during electrical monitoring. Table 1 reports the test results for representative groups.

TABLE 1

Test specimens and results

Figure 3A:
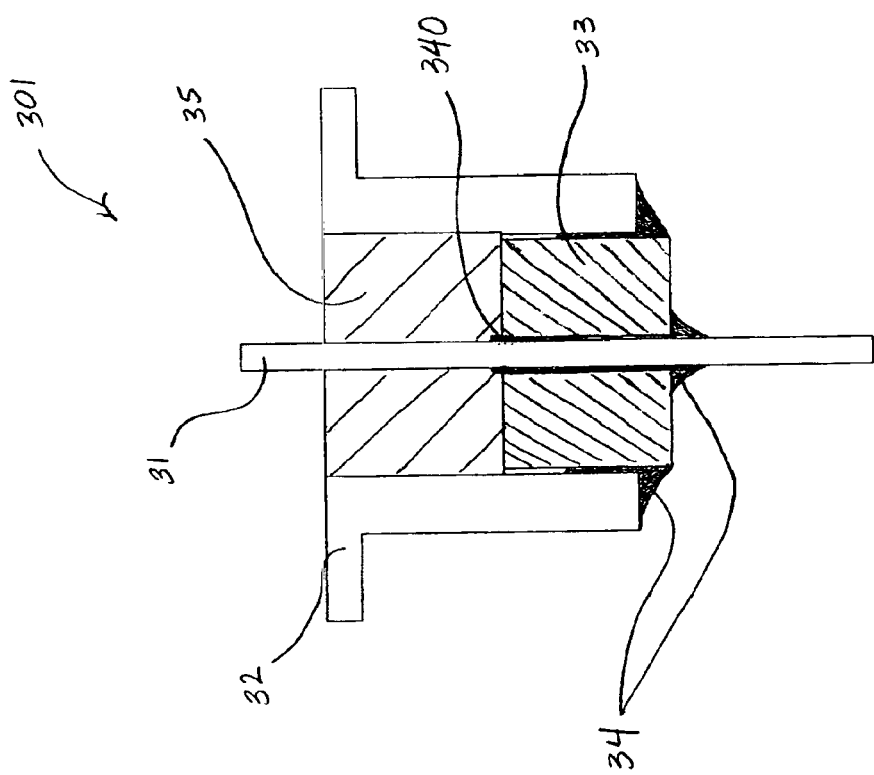
FIG. 3A is a section view of an electrical feedthrough assembly serving as an experimental control.
Figure 3B:
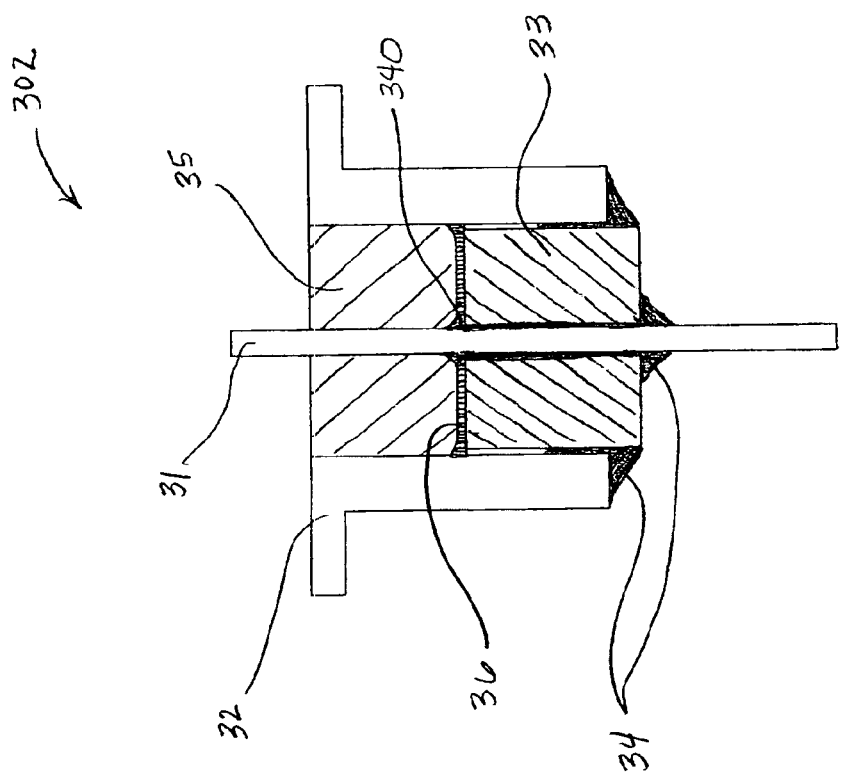
Figure 3D:
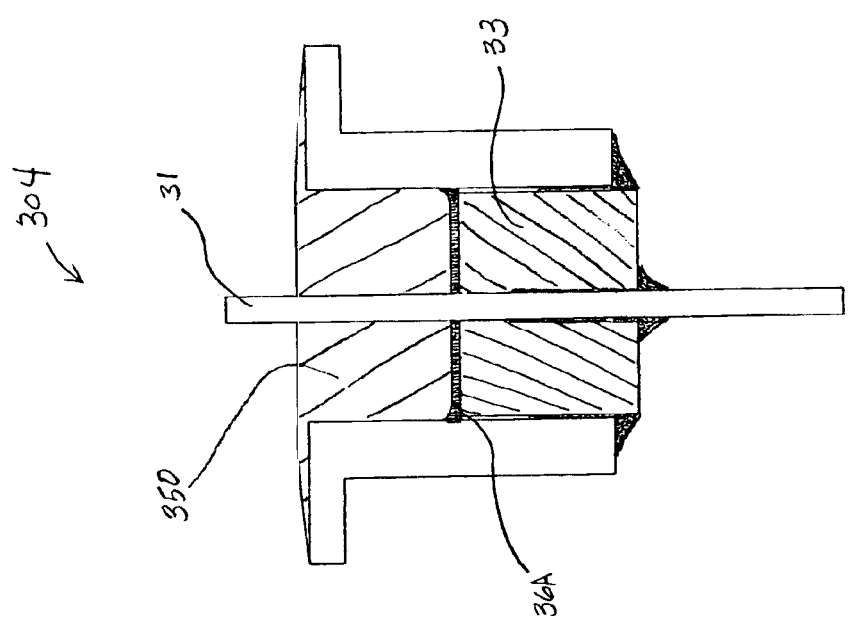
Figure 3E:
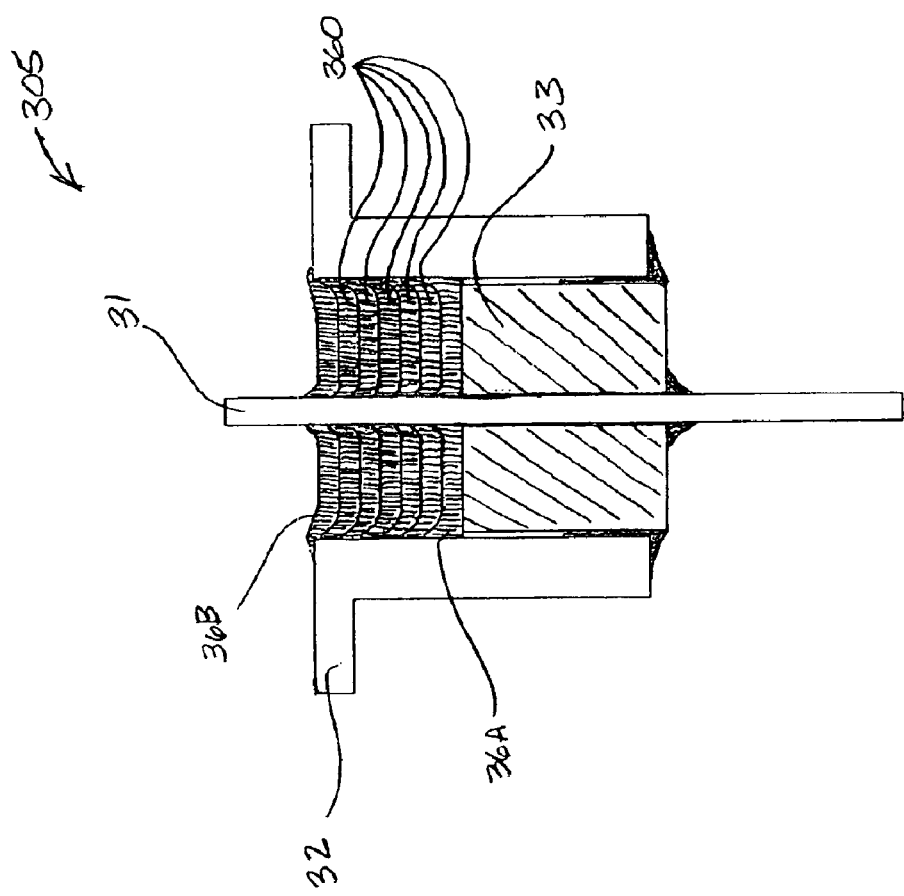

| Figure # for sample configuration/sample group # | Number of samples failing prior to maximum number of test days | Maximum number of test days |
| --- | --- | --- |
| FIG. 3A/group 4 | 2 (at 4 and 59 days) | 369 |
| FIG. 3A/group 8 | 2 (at 2 and 95 days) | 353 |
| FIG. 3B/group 25 | 0 | 365 |
| FIG. 3C/group 2 | 0 | 369 |
| FIG. 3D/group 6.5 | 0 | 369 |
| FIG. 3E/group 3 | 0 | 353 |

FIG. 3A is a section view of an electrical feedthrough 301 representing the experimental control groups 4 and 8, which included a typical backfill layer 35 of Dadet™ epoxy and FIGS. 3B–E are section views of electrical feedthroughs 302–305 representing the alternate embodiments evaluated against the control groups, which included inventive backfills. Each feedthrough assembly 301–305, as illustrated in FIGS. 3A–E, included a niobium terminal pin 31 and a titanium ferrule 32 sealed with sapphire insulator 33 and a gold braze 34.

Braze 34 tends to wick along interfaces between ferrule 32 and insulator 33 and between terminal pin 31 and insulator 33, which in some cases extends beyond top surface of insulator 33, as illustrated as portion 340 of braze 34 in FIGS. 3A–B. Under a continuous DC bias terminal pin 31 is subject to surface oxidization over extended use, which is exacerbated if leak paths develop within backfill layer 35, or at interfaces between backfill layer 35 and terminal pin 31, or at interfaces between backfill layer 35 and ferrule 32 and insulator 33; such leak paths could allow fluids, for example blood or other bodily fluids, to contact pin 31 inside the feedthrough assembly. As a surface of pin 31 is oxidized it becomes more insulative or passivated; such passivation can cause braze 34 to corrode due to an increase in a current density as a result of shunting from the passivated pin to the conductive braze 34. Corrosion of braze 34 is worsened in the event that fluid has leaked into any micro-scale gaps between insulator 33 and terminal pin 31 and, as previously described, corrosion by-products may raise stresses that can induce cracking of insulator 33. It has been determined that failures in control groups 4 and 8 are initiated by fluid leakage past backfill layer 35 which had delaminated from all or one of ferrule 32, pin 31 and insulator 33; delamination of epoxy backfill layers may be caused or exacerbated by downstream manufacturing processes or manipulation of the component including during assembly of the feedthrough and or during implantation.

FIGS. 3B–E illustrate some alternate embodiments, which were evaluated, wherein backfills include at least one coating forming a fluid barrier over insulator 33 and interfaces between insulator 33 and ferrule 32 and insulator 33 and pin 31, the general nature of which was previously described in conjunction with FIG. 2. FIG. 3B, corresponding to group 25, illustrates feedthrough assembly 302 including a coating 36 formed in between insulator 33 and epoxy backfill layer 35 wherein coating further contacts portion 340 of braze 34 in order to form a fluid barrier over braze 34 as well. FIG. 3C, corresponding to group 2, illustrates feedthrough assembly 303 including a backfill including epoxy layer 35 sandwiched in between a first, or bottom coating 36A and a second, or top coating 36B. FIG. 3C further illustrates second coating 36B covering a top surface 38 of ferrule 32 according to one preferred embodiment. FIG. 3D, corresponding to group 6.5, illustrates feedthrough assembly 304 including a backfill including coating 36A formed directly over insulator 33 and a silicone layer 350 formed thereover. FIG. 3E, corresponding to group 3, illustrates feedthrough assembly 305 including a backfill including multiple coatings 360 sandwiched in between bottom coating 36A and top coating 36B.

Each of the coatings depicted in FIGS. 3B-E were formed from a 1:1 (by volume) combination of silicone medical adhesive and heptane which were allowed to air dry at room temperature for greater than 2 minutes before subsequent layers and/or coatings were applied. Backfill layers of Dadet™ epoxy 35, depicted in FIGS. 3A–C, underwent standard curing known to those skilled in the art.

While exemplary embodiments have been presented in the foregoing detailed description, it should be appreciated that a vast number of variations exist. It should also be appreciated that exemplary embodiments are not intended to limit the scope, applicability, or configuration of the invention in any way. Rather, the foregoing detailed description will provide those skilled in the art with a suitable road map for implementing embodiments of the invention. It may be appreciated that various modifications and changes can be made without departing from the scope of the invention as set forth in the appended claims.

What is claimed is:

1. A method for forming a feedthrough assembly for an implantable device having a hermetically sealed container, said feedthrough assembly extending through the container and having a conductive terminal pin, a ferrule surrounding the terminal pin, an insulator within the ferrule, and a backfill of the ferrule exposed to body fluid and disposed over the insulator and around the terminal, comprising the step of: applying a coating to form a fluid barrier over a surface of the insulator, a insulator-to-terminal pin interface and a insulator-to-ferrule interface.

2. The method of claim 1, wherein the coating has a maximum thickness approximately less than or equal to 0.01 inch.

3. The method of claim 2, wherein the maximum thickness is between approximately 0.0001 inch and approximately 0.005 inch.

4. The method of claim 1, wherein the coating comprises a material selected from the group consisting of silicones, polyimides, and fluorosilicones.

5. The method of claim 4, further comprising combining the material with a solvent to form the coating.

6. The method of claim 1, wherein the backfill is a layer of epoxy disposed adjacent the insulator.

7. The method of claim 6, wherein the coating is applied over the layer of epoxy.

8. The method of claim 6, wherein the layer of epoxy is disposed between the insulator and the coating.

9. The method of claim 1, further comprising applying a layer of silicone adjacent the insulator.

10. The method of claim 9, wherein the coating is applied over the insulator and the layer of silicone.

11. The method of claim 9, wherein the layer of silicone is disposed between the insulator and the coating.

12. The method of claim 1, further comprising applying at least one additional coating over the first coating.

13. The method of claim 12, further comprising applying a layer of epoxy adjacent the insulator to form the backfill.

14. The method of claim 13, wherein the coating and the at least one additional coating are applied over the insulator and the layer of epoxy.

15. The method of claim 13, wherein the layer of epoxy is disposed between the insulator and the coating.

16. The method of claim 13, wherein the layer of epoxy is applied between the coating and the at least one additional coating.

17. The method of claim 12, further comprising applying a layer of silicone adjacent the insulator to form the backfill.

18. The method of claim 17, wherein the coating and the at least one additional coating are applied over the insulator and the layer of silicone.

19. The method of claim 17, wherein the layer of silicone is applied between the insulator and the coating.

20. The method of claim 17, wherein the layer of silicone is applied between the insulator and the at least one additional coating.

21. The method of claim 1, wherein the coating contacts a top surface of the ferrule.

22. The method of claim 1, wherein the coating contacts the backfill.

23. The method of claim 1, wherein the coating provides a fluid barrier to the insulator-to-terminal pin interface and the insulator-to-ferrule interface.

* * * * *